US00PP22435P2

(12) United States Plant Patent
Bergman

(10) Patent No.: US PP22,435 P2
(45) Date of Patent: Jan. 3, 2012

(54) ***CHRYSANTHEMUM* PLANT NAMED 'SYNYEL LUCIEN'**

(50) Latin Name: *Chrysanthemum×morifolium*
Varietal Denomination: Synyel Lucien

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/802,502

(22) Filed: Jun. 8, 2010

(51) Int. Cl.
*A01H 5/00* (2006.01)

(52) U.S. Cl. ..... Plt./295

(58) Field of Classification Search ..... Plt./295, Plt./286, 296
See application file for complete search history.

(56) References Cited

PUBLICATIONS

Dana et al. *Chrysanthemums*. Purdue University Cooperative Extension Service, RR 9/96 (1996) HO-77, 2 pages.*

* cited by examiner

*Primary Examiner* — June Hwu
(74) *Attorney, Agent, or Firm* — S. Matthew Edwards

(57) ABSTRACT

A new *Chrysanthemum* plant named 'Synyel Lucien' particularly distinguished by the daisy-type flowers with yellow ray floret color, medium green foliage, fast flowering response time, good stem strength, excellent shelf-life, short and compact fleurette-type plant habit.

1 Drawing Sheet

Latin name of the genus and species of the plant claimed: *Chrysanthemum×morifolium.*

Varietal denomination: 'Synyel Lucien'.

BACKGROUND OF THE NEW PLANT

The present invention comprises a new *Chrysanthemum*, botanically known as *Chrysanthemum×morifolium*, and hereinafter referred to by the variety name 'Synyel Lucien'.

'Synyel Lucien' is a product of a planned breeding program. The new cultivar has daisy-type flowers with yellow ray floret color, medium green foliage, fast flowering response time, good stem strength, excellent shelf-life, short and compact fleurette-type plant habit.

'Synyel Lucien' originated from a hybridization made in May 2004 in a controlled breeding environment in Salinas, Calif. The female parent was the unpatented proprietary plant designated 'YB-A5357', with orange flower color.

The male parent of 'Synyel Lucien' was an unpatented seedling identified as 'YB-A8601' with light bronze flower color. The resultant seed of this cross was sown in September 2004.

'Synyel Lucien' was selected as one flowering plant within the progeny of the stated cross in the March 2005 in a controlled environment in Fort Myers, Fla.

The first act of asexual reproduction of 'Synyel Lucien' was accomplished when vegetative cuttings were propagated from the initial selection in June 2005 in a controlled environment in Fort Myers, Fla.

BRIEF SUMMARY OF INVENTION

Horticultural examination of plants grown from cuttings of the plant initiated in June 2005, and continuing thereafter, has demonstrated that the combination of characteristics as herein disclosed for 'Synyel Lucien' are firmly fixed and are retained through successive generations of asexual reproduction.

'Synyel Lucien' has not been observed under all possible environmental conditions. The phenotype may vary significantly with variations in environment such as temperature, light intensity and day length.

A Plant Breeder's Right for this cultivar was applied for in Canada on Oct. 30, 2009 (#09-6773). 'Synyel Lucien' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synyel Lucien' with colors being as true as possible with an illustration of this type. The photographic drawing shows four flowering plants of the new variety growing in a six inch pot and a close-up of the flowers.

DETAILED BOTANICAL DESCRIPTION

The plant descriptions, measurements and aforementioned photographs were taken in Gilroy, Calif. in April 2010 under natural light. These plants were started and grown in Nipomo, Calif. and bought to Gilroy for descriptions and photographs. Plants were grown under conditions which approximate those generally used in commercial potted *Chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'SYNYEL LUCIEN' AND A SIMILAR VARIETY

| | 'Synyel Lucien' | 'Sunny Yomistique' (U.S. Plant Pat. No. 21,384 |
|---|---|---|
| Flower color: | RHS 3A | RHS 4C |
| Foliage length: | Shorter | Longer |
| Peduncle length: | Longer | Shorter |

Plant:

*Form, growth and habit.*—Herbaceous fleurette pot-type, short and compact habit; stems upright and outwardly spreading; freely branching; short 6.4 week flowering response; suitable for production using no bud removal.

*Plant height.*—About 10 cm.

*Plant height* (*inflorescence included*).—About 14-15 cm.

*Plant width.*—About 18-20 cm.

Roots:

*Number of days to initiate roots.*—4 days at about 22 degrees C.

*Number of days to produce a rooted cutting.*—10 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 137A but a little darker.

*Lower surface.*—RHS 137B to RHS 137C.

*Mature, leaf color, upper surface.*—RHS 137A to RHS 137C.

*Lower surface.*—RHS 137B to RHS 137C.

*Length.*—3.9-4.3 cm.

*Width.*—2.4-2.7 cm.

*Shape.*—Ovate.

*Base shape.*—Attenuate.

*Apex shape.*—Acute.

*Margin.*—Palmately lobed, slightly crenate.

*Texture, upper surface.*—Bi-fid T-shaped hairs.

*Lower surface.*—Bi-fid T-shaped hairs.

*Color of veins, upper surface.*—RHS 144A.

*Color of veins, lower surface.*—Between RHS 144A and RHS 144B.

*Petiole color.*—RHS 144B.

*Length.*—1.0-1.1 cm.

*Diameter.*—0.2 cm.

*Texture.*—Bi-fid T-shaped hairs.

Stem:

*Quantity of main branches per plant.*—3-4.

*Quantity of leaves per branch.*—4-6.

*Color of stem.*—Closest to RHS 146A.

*Length of stem.*—8.0 cm.

*Diameter.*—0.2 cm.

*Length of internodes.*—0.3-0.5 cm.

*Texture.*—Bi-fid T-shaped hairs.

*Color of peduncle.*—Closest to RHS 146A.

*Length of peduncle.*—5.0-6.5 cm.

*Peduncle diameter.*—0.1 cm.

*Texture.*—Bi-fid T-shaped hairs.

Inflorescence:

*Type.*—Composite type, solitary inflorescences (daisy-type) borne terminally above foliage, ray florets arranged acropetally on a capitulum.

*Quantity of short days to flowering* (*response time*).—38-44 days.

*Quantity of inflorescences per plant.*—About 50.

*Lastingness of individual blooms on the plant.*—About 28 days.

*Fragrance.*—Slight.

Bud (just before opening/showing color):

*Color.*—RHS 3A.

*Length.*—0.5 cm.

*Width.*—0.7-0.9 cm.

*Shape.*—Oblate.

Immature inflorescence:

*Diameter.*—1.3-2.5 cm.

*Color of ray florets, upper surface.*—RHS 3A.

*Lower surface.*—RHS 3C.

Mature inflorescence:

*Diameter.*—3.3-3.5 cm.

*Depth.*—0.6 cm.

*Total diameter of 'disc'.*—1.3-1.5 cm.

*Receptacle height.*—0.5 cm.

*Receptacle diameter.*—0.4-0.5 cm.

Ray florets:

*Average quantity of florets.*—About 40 in numerous whorls.

*Color of florets, upper surface.*—RHS 3A.

*Lower surface.*—RHS 3C.

*Length.*—1.4-1.5 cm.

*Width.*—0.4-0.5 cm.

*Shape.*—Elliptical.

*Apex shape.*—Emarginated to praemorse.

*Margin.*—Entire.

*Texture, upper surface.*—Papillose.

*Lower surface.*—Papillose.

Disc florets:

*Average quantity of floret.*—100-120.

*Color of florets.*—RHS 155C but more green with a RHS 1C apex.

*Length.*—0.4 cm.

*Width.*—0.1.

*Shape.*—Tubular, elongated.

*Apex shape.*—Acute, 5 pointed.

Phyllaries:

*Quantity.*—About 20-25.

*Color, upper surface.*—Closest to RHS 137A.

*Lower surface.*—Between RHS 137A and RHS 137B.

*Length.*—0.4 cm.

*Width.*—0.1-0.15 cm.

*Shape.*—Ovate.

*Apex shape.*—Acute.

*Based.*—Fused.

*Margins.*—Entire, papery.

*Texture, upper surface.*—Glabrous, smooth.

*Lower surface.*—Bi-fid T-shaped hairs, pilose.

Reproductive organs:

Found on both florets:

*Pistil.*—1.

*Length.*—0.4-0.5 cm.

*Style color.*—RHS 155C but more green.

*Style length.*—0.4 cm.

*Stigma color.*—RHS 7C.

*Stigma shape.*—Bi-parted.

*Ovary color.*—Not observed.

Found on only disc florets:

*Stamens.*—1.

*Color of filaments.*—RHS 155C but more green.

*Length filaments.*—0.3 cm.
*Anther color.*—RHS 13B.
*Anther length.*—0.15 cm.
*Anther shape.*—Oval.
*Color of pollen.*—About RHS 13A.
*Pollen amount.*—Poor.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Synyel Lucien' substantially as illustrated and described herein.

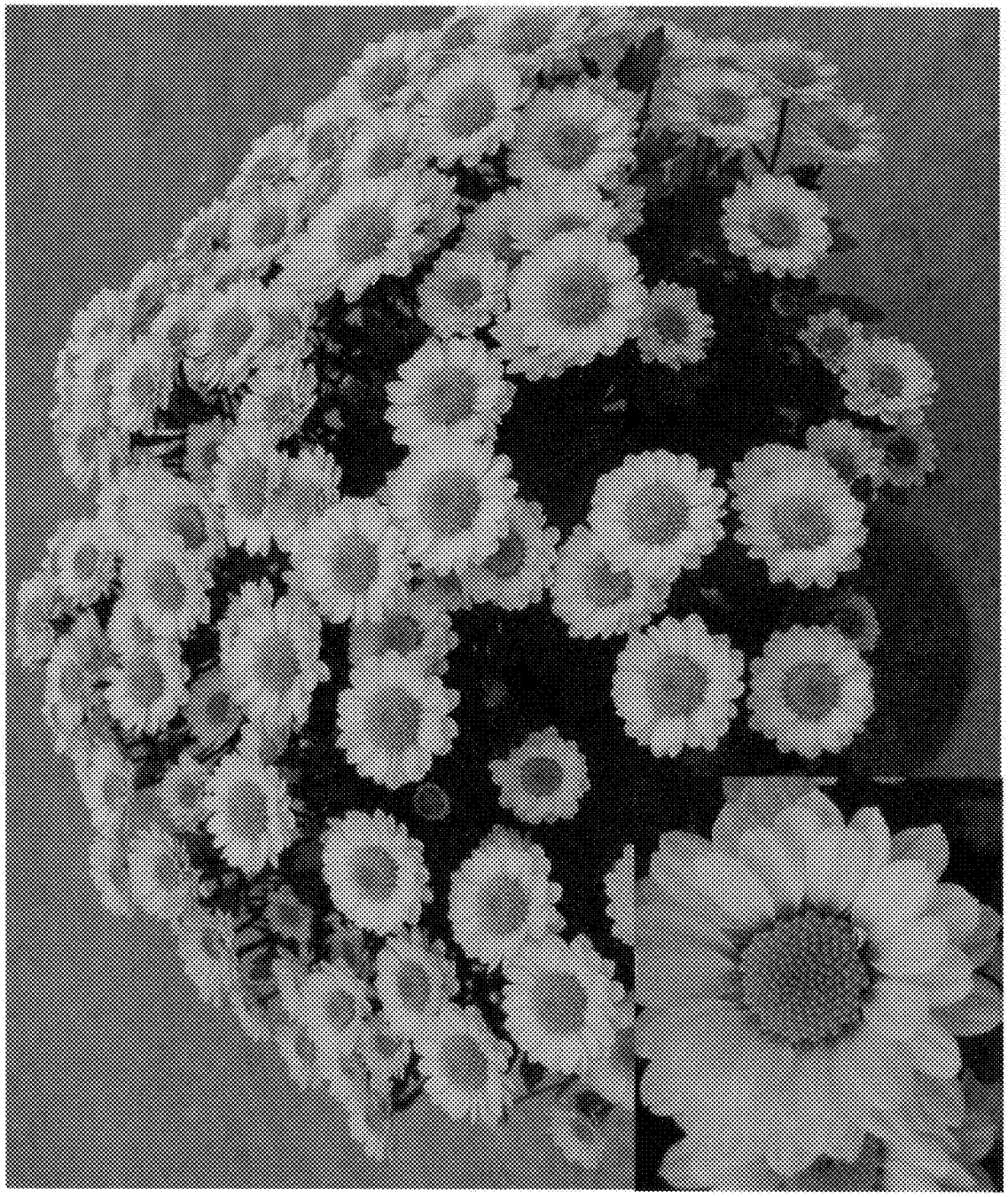

* * * * *